United States Patent [19]

Ferrua et al.

[11] Patent Number: 5,010,017
[45] Date of Patent: Apr. 23, 1991

[54] PROCESS FOR THE IMMUNOLOGICAL QUANTITATIVE DETERMINATION OF $T_3$ AND/OR $T_4$ THYROID HORMONES, USING THYROGLOBULIN

[75] Inventors: Bernard Ferrua, Nice; Claude Moulin, Bagnols sur Ceze, both of France

[73] Assignee: Compagnie Oris Industrie S.A., France

[21] Appl. No.: 569,396

[22] Filed: Aug. 17, 1990

Related U.S. Application Data

[62] Division of Ser. No. 48,060, May 11, 1989, Pat. No. 4,966,838.

[30] Foreign Application Priority Data

May 12, 1986 [FR] France ................. 86 06763

[51] Int. Cl.⁵ .................. G01N 33/53; C12Q 1/00
[52] U.S. Cl. ..................... 436/500; 435/7.8; 435/7.93; 435/975
[58] Field of Search ................. 435/7; 436/500

[56] References Cited

U.S. PATENT DOCUMENTS 4,966,838 10/1990 Ferrua et al. ................. 435/7

Primary Examiner—Robert A. Wax
Assistant Examiner—Bradley L. Sisson
Attorney, Agent, or Firm—Michael N. Meller

[57] ABSTRACT

The invention relates to a process for the immunological quantitative determination of the $T_3$ and/or $T_4$ thyroid hormones.

In a process for the immunological quantitative determination of $T_4$ thyroxine and/or $T_3$ triiodothyronine present in free form in a sample, $T_3$ and/or $T_4$ to be determined are put into competition with thyroglobulin for the sites of anti-$T_3$ and/or anti-$T_4$ antibodies present in a limited quantity, whereafter a determination is made of either the quantity of thyroglobulin fixed to the anti-$T_3$ and/or anti-$T_4$ antibodies, or the quantity of thyroglobulin not fixed to the anti-$T_3$ and/or anti-$T_4$ antibodies.

Application to the determination of the total $T_3$ and/or $T_4$ of a biological sample.

5 Claims, 4 Drawing Sheets

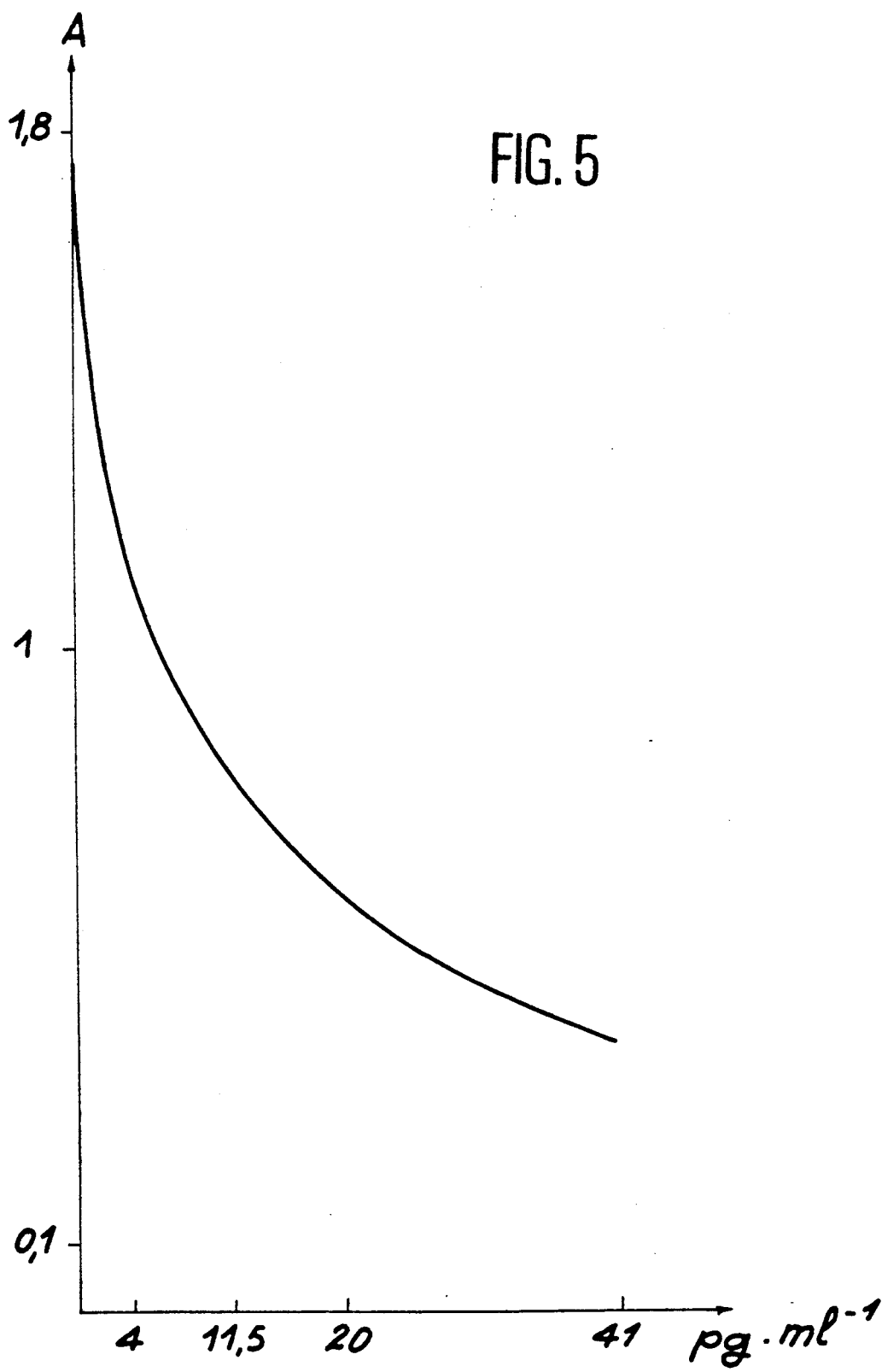

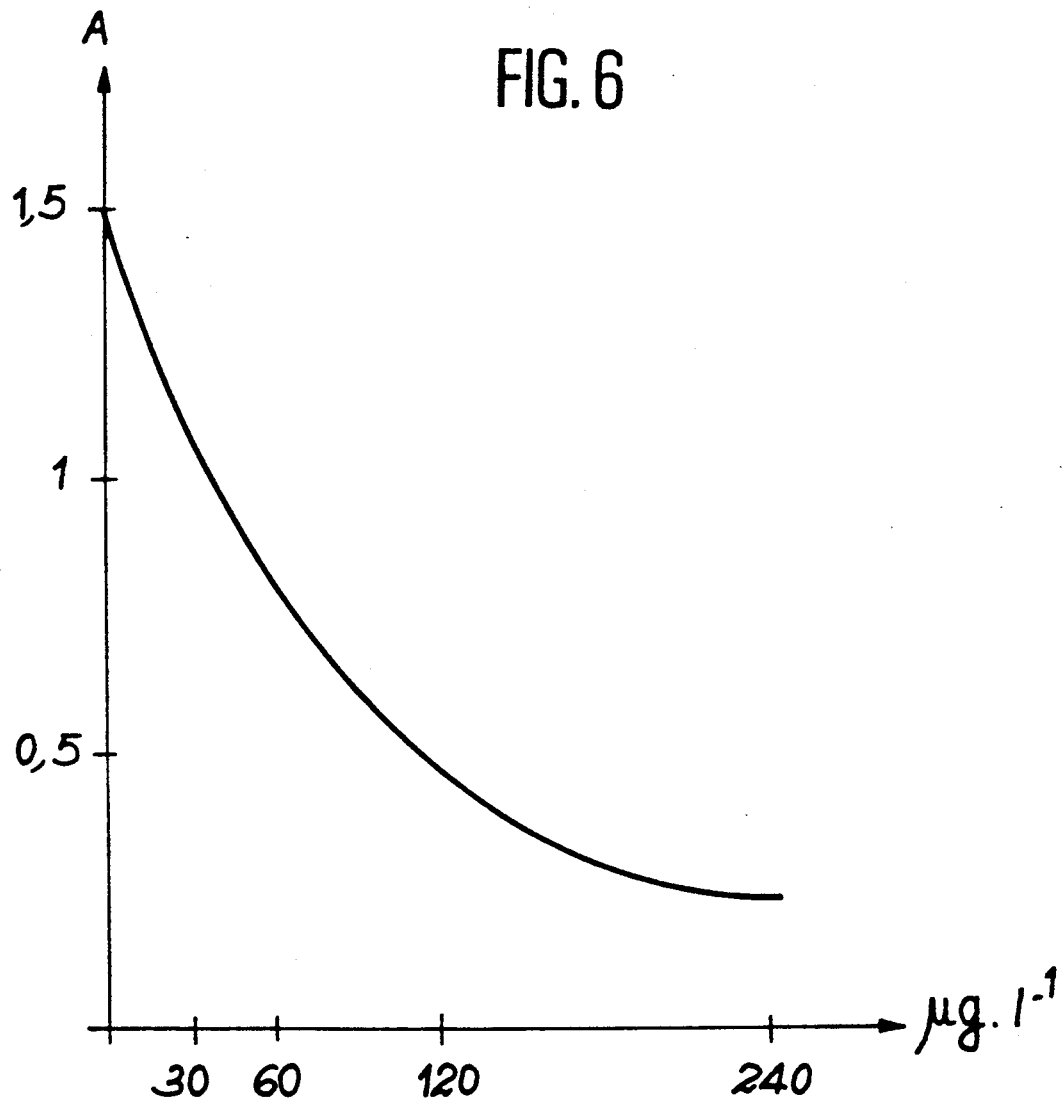

PROCESS FOR THE IMMUNOLOGICAL QUANTITATIVE DETERMINATION OF $T_3$ AND/OR $T_4$ THYROID HORMONES, USING THYROGLOBULIN

This is a divisional of U.S. Ser. No. 048,060 filed May 11, 1989, now U.S. Pat. No. 4,966,838.

The present invention relates to a process for the immunological quantitative determination of the $T_3$ and/or $T_4$ thyroid hormones.

BACKGROUND OF THE INVENTION

The thyroid gland is an endorine gland situated at the base of the neck which synthesizes two peptidic hormones, $T_3$ triiodothyronine and $T_4$ thyroxine, by the condensation of two molecules of iodized thyrosine, namely monoiodothyrosine and diiodothyrosine.

The synthesis takes place from a thyroid protein, thyroglobulin, which is also the reserve form of the thyroid hormones. These hormones are released into the circulation by a proteolytic process, the hormones being conveyed by three seric proteins: TBG (thyroxine-bonding globulin), TBPA (thyroxine-bonding prealbumin) and albumin. However, the free and bonded forms of the hormones exist in the blood in a state of dynamic equilibrium governed by the law of mass action.

The thyroid hormones exert their activity on the majority of tissues, except the brain. For example, they stimulate the oxygen consumption of the majority of cells, take part in regulating the metabolism of the lipids and glucids and are necessary for the development of normal growth. However, it is generally assumed that only the free forms of the hormone are biologically active and can enter the cells to exert their physiological action.

Processes allowing the quantitative determination not only of the total concentration of the $T_3$ and $T_4$ hormones but also of the concentration of these hormones in free form are very advantageous for diagnosing hyperthyroidism or hypothyroidism, since the determination of the total $T_4$ and/or $T_3$ rate may lead to errors in the diagnosis of hyperthyroidism or hypothyroidism caused by an alteration in the transporting proteins. The fact is that the concentration of bonding proteins may increase, for example, during pregnancy, liver diseases and when oestrogens or opiates are taken, in which case the total $T_4$ or $T_3$ rate increase, at the same time, and this may lead to a diagnosis of hyperthyroidism, although the rates of free $T_3$ or $T_4$ are normal and so is the patient's thyroid gland.

Conversely, the total $T_3$ or $T_4$ rate can be reduced by a reduction in the rate of the bonding proteins, and this might lead to a diagnosis of hypothyroidism, although the rate of free $T_3$ or $T_4$ is normal.

It is therefore preferably to be able to determine the rates of free $T_3$ or $T_4$ to better appreciate the condition of the patient, since such rates can be determined either directly or from the total $T_3$ and $T_4$ concentrations and the index of saturation of the carrier proteins.

Low rates of the $T_3$ and $T_4$ thyroid hormones found in human or animal sera require the use of sensitive methods of quantitative determination.

The methods currently used for quantitative determinations of this kind adopt immunological techniques, including, first of all, radio-immunological quantitative determinations using $T_4$ or $T_3$ labelled with iodine[125].

More recently, techniques have been developed for enzyme-immunological quantitative determination, in either the heterogeneous or homogeneous phase.

The methods in the homogeneous phase include quantitative determinations based on the polarization of fluorescence, the transfer of fluorescence or an inhibition of the enzyme. These determinations have the advantage that they can be completely automated, but they require the use of sophisticated equipment.

The methods in the heterogeneous phase include a process for the determination of the free or total $T_3$ or $T_1$ which consists in bringing into competition $T_3$ or $T_4$ and a known quantity of $T_3$ or $T_4$ labelled with an enzyme for a limited number of specific antibody sites of the hormone (H. V. Weetall et al., Clin. Chem., Vol. 28, no. 4 (1982), pp. 666-671; SCHALL et al, Clin. Chem., 1978, 24, 1801-1804; and ALBERT et al., Ed. S. B. Pal, 1978, pp. 153-174). To perform the same kind of determination in the heterogeneous phase, the hormone to be determined and a predetermined quantity of hormone fixed on a solid support might be put into competition for a limited quantity of active sites of a labelled antibody specific to the hormone. (Masao Ito et al., Clin. Chem., 30/10, 1682-1685 (1984) and Gnemmi et al., Enzyme Labelled Immunoassay of Hormones and Drugs, 1978, Walter de Gruyter and Co., Berlin-New-York).

However, these two methods of quantitative determination in the heterogeneous phase are difficult to implement with the $T_3$ and $T_4$ hormones, which generally lose their antigen activity when they are fixed on a solid support, or their biological and/or antigen activity when they are coupled with a macromolecule. Moreover, when this method is to be used for the quantitative determination of $T_3$ and/or $T_4$ in the free form, the labelled $T_3$ and/or $T_4$ molecules must not be recognized by the proteins transporting the $T_3$ and $T_4$ hormones.

On the other hand, the determination might be made by coupling the $T_3$ or $T_4$ hormone with a powder, but in that case, the performance of the determination raises problems of washing.

SUMMARY OF THE INVENTION

The invention relates precisely to a process for the immunological quantitative determination of the $T_3$ and/or $T_4$ thyroid hormones which enables the aforedescribed problems to be solved.

According to the invention, the process for the immunological quantitative determination of $T_4$ thyroxine and/or $T_3$ triiodothyronine present in free form—i.e., not bonded to carrier proteins—in a reaction medium, is characterized in that it consists in putting $T_3$ and/or $T_4$ to be determined into competition with thyroglobulin for the sites of anti-$T_3$ and/or anti-$T_4$ antibodies present in limited quantity, and in then determining either the quantity of thyroglobulin fixed to the anti-$T_3$ and/or anti-$T_4$ antibodies, or the quantity of thyroglobulin not fixed to the anti-$T_3$ and/or anti-$T_4$ antibodies.

In what follows, the expression "in free form" applied to $T_3$ and $T_4$ means that the reference is to $T_3$ and $T_4$ not bonded to carrier proteins. It also applies both to the determination of free $T_3$ or $T_4$ and to determination of total $T_3$ or $T_4$, as known in the literature.

The process according to the invention thus consists in using thyroglobulin as a competitor for the competitive reaction relating to the antibody sites. This provides many advantages, since thyroglobulin can be fixed on a solid phase or be coupled to a labelling molecule or atom, while still being recognized by the anti-$T_3$ and anti-$T_4$ antibodies. Moreover, determination is not disturbed by the proteins transporting $T_3$ and $T_4$ hormones, since the competitor used is thyroglobulin, instead of labelled $T_3$ and/or $T_4$ hormones or labelled antibodies.

Thyroglobulin is a glycoprotein of complex structure which is the starting product for the synthesis of the $T_3$ and $T_4$ hormones and therefore contains the sequences of these hormones. However, it could not be supposed that in this complex structure these sequences would be recognized by specific antibodies of the $T_3$ and $T_4$ hormones, since studies relating to the structure of thyroglobulin, such as that published by C. Marriq et al. in Eur. J. Biochem. 111, 33–47 (1980) simply showed that in this structure several sites of formation of the $T_3$ and $T_4$ hormones existed and that there was no doubt that biosynthesis of the $T_3$ hormone could take place only in a clearly delimited zone of the molecule, while the biosynthesis of the $T_4$ hormone might take place at a larger number of sites. The results of that study showed that thyroglobulin had no reactivity in relation to anti-$T_3$ or anti-$T_4$ antibodies.

In the process according to the invention use can be made of thyroglobulin originating from different animal species, for example, thyroglobulin coming from bovine or porcine animals.

Moreover, the thyroglobulin can be used in different forms, for example in the monomeric, native, denatured, polymerized or hydrolyzed form.

The process according to the invention can be used to determine either the total $T_4$ or $T_3$ concentration of a biological sample, or the free $T_4$ or $T_3$ concentration thereof, since, as was already shown, the process of determination according to the invention enables free $T_3$ and/or $T_4$ to be determined. However, if the total $T_4$ or $T_3$ concentration of a sample is to be determined, the sample is subjected to a treatment to release the $T_3$ and $T_4$ hormones bonded to sample-carrying proteins. The treatment may consist in the addition of an inhibitor of the bond between $T_3$ and/or $T_4$ and their carrier proteins, such inhibitor being, for example, salicylic acid, merthiolate or 8-anilino-1-naphthalene sulphonic acid. By means of this treatment the sample can be used directly in the quantitative determination process according to the invention.

Also in what follows the quantitative determination of $T_3$ and/or $T_4$ will mean both the determination of the total $T_3$ and/or $T_4$ concentration and the determination of the free $T_3$ and/or $T_4$ concentration.

To put the process according to the invention into effect, first of all a competitive reaction is performed between the $T_3$ and/or $T_4$ to be determined and thyroglobulin for the sites of the anti-$T_3$ and/or anti-$T_4$ antibodies present in a limited quantity. For the purpose of this reaction, therefore, we obtain thyroglobulin bonded to the antibodies, $T_3$ and/or $T_4$ bonded to the antibodies and free thyroglobulin and free $T_3$ and/or $T_4$. The quantity of thyroglobulin bonded to the antibodies depends on the quantity of $T_4$ and/or $T_3$ present in the sample and such quantity of bonded thyroglobulin diminishes when the quantity of $T_4$ and/or $T_3$ increases. To determine the quantity of $T_4$ and/or $T_3$ present in the sample, therefore, we determine the quantity of thyroglobulin bonded to the antibodies or the quantity of thyroglobulin in the free form.

The determination can be performed by the conventional methods used in immunological quantitative determination, such methods employing either the labelling of one of the components used for the competition reaction, for example, in this case thyroglobulin or the anti-$T_3$ and/or anti-$T_4$ antibodies, or the use of additional labelled compounds which are capable of becoming fixed on the thyroglobulin bonded to the antibodies or free thyroglobulin.

As a rule these additional compounds are formed by specific labelled antibodies of the $\gamma$-globulins of the species which produced the anti-$T_3$ and/or anti-$T_4$ antibodies, with labelled anti-thyroglobulin or anti-$T_4$ and/or anti-$T_3$ antibodies. The additional compounds used can therefore be systems comprising a labelled compound and a protein, for example, the labelled biotinylated/avidin antibody systems, using also biotinylated anti-$T_3$ and/or anti-$T_4$ antibodies in the determination. For such determination the thyroglobulin or the different antibodies are labelled by conventional methods.

Also in what follows the term "labelled" applied to thyroglobulin or different types of antibodies means that the thyroglobulin or antibodies have been modified by a labelling element which can be, for example, a radioactive element, a fluorescent element, a luminescent element, an enzyme, a fluorescent chromophore, a light absorbing chromophore, biotin, etc.

To more readily perform mass determination of the quantity of thyroglobulin bonded to the antibodies or of thyroglobulin in free form, use can be made of the conventional determination methods in the heterogeneous phase which enable the thyroglobulin bonded to the antibodies to be separated from the free thyroglobulin.

However, quantity-determining methods in the homogeneous phase which do not comprise such a separation can also be used according to the invention.

When quantitative determination is performed in the heterogeneous phase, a solid phase is used, on which either the thyroglobulin, or the anti-$T_3$ and/or anti-$T_4$ antibodies are immobilized.

The solid phases which can be used can be of different kinds. For example, use can be made of macroscopic solid phases, formed by tubes, balls or fins made from polymer or other materials.

The polymers which can be used are, for example, polystyrene, the polyamides, polypropylene, polyoxy methylene and the styrene copolymers.

Use can also be made of finely divided microscopic solid phases containing thyroglobulin or anti-$T_3$ or anti-$T_4$ antibodies, for example, powders, aggregates of polymer, protein or other materials. Such phases can be formed by thyroglobulin or anti-$T_3$ or anti-$T_4$ antibodies made insoluble by physicochemical or immunological processes. These macroscopic phases can be obtained, for example, by forming in the reaction medium a precipitate formed by a network of anti-IgG and IgG antibodies originating from the same species as the anti-$T_3$ and/or anti-$T_4$ antibodies used for determination, such network being able to retain the thyroglobulin/anti-$T_3$, thyroglobulin/anti-$T_4$, $T_3$/anti-$T_3$ and/or $T_4$/anti-$T_4$ complexes. The network can, for example, be formed by rabbit anti-IgG and rabbit IgG sheep antiserum if the anti-$T_3$ and/or anti-$T_4$ antibodies originate from rabbits.

If finely divided solid phases are to be used, the solid phase can be separated from the liquid medium in which the competitive reaction has been performed by conventional techniques, for example, centrifugation.

In contrast, if solid phases of the kind of tubes, balls or fins are used, the separation process is simpler, more particularly when such solid phases are unitary with the tubes in which the reaction is to be performed.

DESCRIPTION OF PREFERRED EMBODIMENTS

Various embodiments of the quantitative determination according to the invention in the heterogeneous phase will now be described.

I. Determinations in the Heterogeneous Phase with Thyroglobulin Immobilized on a Solid Phase To perform these determinations, as a rule the thyroglobulin is fixed on the aforedescribed solid phases by using a solution of thyroglobulin, for example, bovine or porcine thyroglobulin which is contacted with the solid phase for a sufficient period, which may range from one hour to one night, at various temperatures, so as to fix the required quantity of thyroglobulin. This quantity depends more particularly on the contact time and temperature used.

The solid phases on which the thyroglobulin is immobilized can be used to determine triiodothyronine and thyroxine separately or simultaneously.

To determine $T_4$ thyroxine on its own, the $T_4$-containing sample to be determined is brought into contact with the immobilized thyroglobulin and a limited quantity of an anti-$T_4$ antibody, and then the quantity of anti-$T_4$ antibody fixed to the immobilized thyroglobulin is determined.

To determine $T_3$ triiodothyronine on its own, the triiodothyronine-containing sample to be determined is brought into contact with the immobilized thyroglobulin and a limited quantity of anti-$T_3$ antibodies, and then the quantity of anti-$T_3$ antibodies fixed to the immobilized thyroglobulin is determined.

In both cases, the quantity of anti-$T_4$ or anti-$T_3$ antibodies fixed to the immobilized thyroglobulin can readily be determined by using labelled monoclonal or polyclonal anti-$T_3$ and/or anti-$T_4$ antibodies or their fragments as the antibodies.

Preferably the marker used is an enzyme, such as horse-radish peroxidase, which can readily be coupled to the antibodies used and whose enzymatic activity can be determined in satisfactory conditions by very simple colorimetric methods.

Other enzymes can also be used, for example, $\beta$-galactosidase or an alkaline phosphatase.

In the two determinations described below, use can also be made of a second antibody to develop the quantity of anti-$T_3$ or anti-$T_4$ antibodies fixed on the immobilized thyroglobulin, or the quantity of thyroglobulin which is not bonded to the anti-$T_3$ or anti-$T_4$ antibodies.

In that case the anti-$T_3$ or anti-$T_4$ antibodies form a first antibody, and a second labelled antibody is used which is able to be fixed on the first antibody or the thyroglobulin. By way of example, the second antibody can be a labelled anti-$T_3$ or $T_4$ which will be fixed on the $T_3$ or $T_4$ sites of the thyroglobulin which did not react.

In this way the reaction of the $T_3$ or $T_4$ with the anti-$T_3$ or anti-$T_4$ antibodies is not disturbed, since there is no need to modify such antibodies chemically to label them.

However, in one variant embodiment adapted to the use of fluorescent labels, the first antibody can be labelled by a fluorescent chromophore and the second antibody by a light-absorbing chromophore, so as to detect the quantity of antibodies fixed on the thyroglobulin by the extinction of the fluorescence reaction, using the method disclosed in U.S. Pat. No. 4,174,384.

To determine $T_4$ thyroxine and $T_3$ triiodothyronine simultaneously, the $T_3$- and $T_4$-containing sample to be determined is brought into contact with the thyroglobulin and limited quantities of anti-$T_3$ antibodies and anti-$T_4$ antibodies, and then a determination is made of the quantity of anti-$T_3$ antibodies fixed to the thyroglobulin, and the quantity of anti-$T_4$ antibodies fixed to the thyroglobulin.

In this case, as previously, use can be made of labelled anti-$T_3$ and anti-$T_4$ antibodies, but they must be labelled with different atoms and/or molecules.

By way of example, the anti-$T_3$ antibodies can be labelled with $\beta$-galactosidase and the anti-$T_4$ antibodies can be labelled with an alkaline phosphatase, or vice versa, as described by C. Blake et al. in Clinical Chemistry, Vol. 28, No. 7, (1982), pp. 1469–1473.

In the latter determination, the quantities of anti-$T_3$ and anti-$T_4$ antibodies fixed on the thyroglobulin can also be revealed by using a second group of labelled antibodies. In that case the anti-$T_3$ and anti-$T_4$ antibodies respectively, and a third labelled antibody is used which is able to be fixed specifically on the first anti-$T_3$ antibody, a fourth labelled antibody also being used which is able to be fixed specifically on the second anti-$T_4$ antibody, the third and fourth antibodies being labelled differently.

In this case the labels used can be more particularly enzymes, for example, the pair formed by $\beta$-galactosidase and alkaline phosphatase.

II. Determination in Heterogeneous Phase with Antibodies Immobilized on a Solid Phase In these determinations the antibodies are fixed on a solid phase which can be formed as previously by a macroscopic or microscopic phase of polymer or other materials, and the mobilized antibodies can be used to determine triiodothyronine and thyroxine separately or simultaneously.

In this case the determination method is the same, but in order to be able to determine the quantity of thyroglobulin fixed to the anti-$T_3$ and/or anti-$T_4$ antibodies, conveniently use can be made either of a second group of labelled antibodies capable of being fixed specifically on some other reactive site of the thyroglobulin or labelled thyroglobulin.

When a second group of antibodies is used, they can be formed by labelled anti-$T_3$ antibodies and/or labelled anti-$T_4$ antibodies, which are capable of being fixed specifically on some other reactive site of the thyroglobulin.

In the first case, which is adapted to the immonological quantitative determination of $T_4$ thyroxine, the thyroxine to be determined is brought into contact with the thyroglobulin, a limited quantity of anti-$T_4$ antibody is fixed on a solid phase and labelled anti-$T_3$ and/or anti-$T_4$ antibodies, and then determination is made of the quantity of labelled anti-$T_3$ and/or anti-$T_4$ antibodies fixed on the solid support via the thyroglobulin.

If the process is intended for the immunological quantitative determination of $T_3$ triiodothyronine, the triiodothyronine to be determined is brought into contact with thyroglobulin, a limited quantity of anti-$T_3$ antibodies fixed on a solid phase and labelled anti-$T_4$ and/or anti-$T_3$ antibodies, and a determination is performed of the quantity of marked anti-$T_4$ and/or anti-$T_3$ antibodies fixed on the solid support via the thyroglobulin.

When labelled thyroglobulin is used, the liquid sample containing the $T_4$ thyroxine (or the $T_3$ triiodothyronine) to be determined is brought into contact with labelled thyroglobulin and anti-$T_4$ or anti-$T_3$ antibodies immobilized on a solid support, whereafter the quantity of labelled thyroglobulin fixed on such support is determined.

Preferably, use is made of thyroglobulin labelled with an enzyme which can be coupled to the thyroglobulin either directly or via an anti-thyroglobulin antibody—i.e., a conjugated thyroglobulin antibody/anti-thyroglobulin-enzyme compound.

The two kinds of determination in the heterogeneous phase described above can be performed with conventional devices, more particularly with tubes containing a solid phase which can either be the wall of the tube itself, or be inserted into the tube, for example, in the form of a finned device, as disclosed in European Patent Application EP-A-0 097 573 filed in the name of C.E.A. on June 9, 1983.

For these determinations, first of all the thyroglobulin (or the anti-$T_3$ and/or anti-$T_4$ antibodies) are fixed on the solid phase, and then the liquid sample to be determined and the anti-$T_3$ and/or anti-$T_4$ antibodies (or thyroglobulin) are introduced into the tube.

The $T_3$ and/or $T_4$ present in the sample and the thyroglobulin enter into competition for the antibody sites and a certain proportion of antibodies is fixed on the immobilized thyroglobulin (or a proportion of the thyroglobulin is fixed on the immobilized antibodies). After this operation, the liquid phase is eliminated from the tube, whereafter the solid phase is washed and the quantity of antibodies fixed on the solid phase (or the quantity of thyroglobulin fixed on the solid phase) is determined, using the conventional developing methods described hereinbefore, or using labelled anti-$T_3$ and/or anti-$T_4$ antibodies (or labelled thyroglobulin), or using a second group of labelled antibodies.

When use is made of a second group of labelled antibodies, they can be added either during the competitive reaction, or after the operation of washing the solid phase.

For each type of determination these operations are performed on samples containing known quantities of $T_3$ and/or $T_4$, so as to establish a calibration curve, reference then being made to the calibration curve to determine the $T_3$ and/or $T_4$ content of a sample.

The invention also relates to a kit for performing the quantitative determination in the heterogeneous phase of $T_4$ thyroxine, using only one antibody.

The kit comprises:
a series of tubes each comprising a solid phase coated with thyroglobulin in the same conditions,
a series of flasks containing standard samples of $T_4$ thyroxine, and
a flask containing a labelled anti-$T_4$ antibody.

Preferably the labelled anti-$T_4$ antibody is formed by a conjugated compound of monoclonal anti-$T_4$ antibody and an enzyme such as horse-radish peroxidase.

In that case the kit also comprises:
at least one flask containing a chromogen for enzymatic development,
a flask containing a substrate buffer for enzymatic development, and
a flask containing an acid able to stop the enzymatic reaction.

The chromogen used for the enzymatic development can be the bis-chlorohydrate of o-phenylene diamine and the acid able to stop the enzymatic reaction can be oxalic acid.

By way of example, the following is the composition of a kit of this kind:
64 ELSA tubes comprising a solid phase of fin type on which the thyroglobulin is fixed,
2 flasks of a conjugated compound of monoclonal anti-$T_4$ antibody coupled to horse-radish peroxidase,
5 flasks of standard samples of lyophilized $T_4$ covering the range 0 to 50 pg/ml,
2 flasks of control sera containing lyophilized $T_4$,
2 flasks of lyophilized chromogen, each flask containing 32 mg of 2 HCl orthophenylene diamine in a saline medium,
1 flask of substrate buffer containing 32 ml of buffer with 0.02% of $H_2O_2$ and a preservative, and
2 sachets each containing 3.15 g of powdered oxalic acid.

A kit of the same kind can be made for determining $T_3$ triiodothyronine, using the same constituents, except that the labelled anti-$T_4$ antibody is replaced by a labelled anti-$T_3$ antibody, which can also be a conjugated compound of anti-$T_3$ antibody and an enzyme.

III. Determinations in the Homogeneous Phase

According to the invention thyroxine or triiodothyronine can also be determined in the homogeneous phase by using the same competitive reaction between the $T_3$ or $T_4$ to be determined and thyroglobulin. In that case, for example, three different modes of operation can be used.

In a first operating mode use is made of thyroglobulin labelled with an enzyme such as maleate dehydrogenase, which exhibits the property of having a lower enzymatic activity when it is coupled with thyroglobulin. In contrast, the fixation of an anti-$T_4$ antibody on the thyroglobulin/maleate dehydrogenase complex partially re-establishes the initial activity. As a result, determination can be performed in the homogeneous phase, since the enzymatic activity will decrease in dependence on the quantity of $T_4$ or $T_3$ present in the sample to be determined. In that case the conjugated thyroglobulin/maleate dehydrogenase compound, the anti-$T_4$ (or anti-$T_3$) antibody is brought into contact with the sample containing the hormone $T_4$ (or $T_3$) to be determined and the substrate enabling the enzymatic activity to be determined (maleic acid). Then a kinetics measurement is directly made in the reactional mixture over a time fixed by measurement at 340 nm, corresponding to the appearance of NADH.

In a second operating mode use is made of thyroglobulin coupled to a phosphonate capable of irreversibly inhibiting acetyl cholinesterase where it is not combined with an anti-$T_4$ (or anti-$T_3$) antibody. In that case the sample to be determined is brought into contact with the thyroglobulin coupled to the phosphonate and a limited quantity of anti-$T_4$ (or anti-$T_3$) antibodies. In this way the thyroglobulin/phosphonate anti-$T_4$ (anti-$T_3$) complexes are partly dissociated and the thyroglobulin/phosphonate exerts its inhibiting action. Then the quantity of thyroglobulin/phosphonate fixed to the anti-$T_4$ (or anti-$T_3$) antibodies is determined by developing, using a colorimetric method, the quantity of acetyl cholinesterase inhibited, by using as the substrate the iodide of a acetyl $\beta$-(methyl thiocholine) and performing reading at 415 nm.

In a third operating mode, use is made of thyroglobulin coupled to a fluorochrome, such as fluorescein, whose fluorescence increases when the compound is coupled to the corresponding antibody. In this case the sample to be determined is brought into contact with the thyroglobulin labelled with fluorescein and anti-$T_4$ (or anti-$T_3$) antibodies, whereafter a determination is made of the fluorescence polarization of the reaction mixture, which is inversely proportional to the quantity of $T_4$ (or $T_3$) to be determined fixed to the thyroglobulin/fluorescein compound.

The invention also relates to a process for fixing anti-$T_3$ and/or anti-$T_4$ antibodies on a solid support which can be used more particularly to purify the anti-$T_3$ and/or anti-$T_4$ antibodies.

This process of fixing anti-$T_3$ and/or anti-$T_4$ antibodies on a solid support consists in first fixing thyroglobulin on such support, and then bringing the support, on which the thyroglobulin is fixed, into contact with a solution of such anti-$T_3$ and/or anti-$T_4$ antibodies.

Such a solid support can also be used to purify the anti-$T_3$ and/or anti-$T_4$ antibodies, since it is enough to bring a solution containing such antibodies into contact with a solid support on which thyroglobulin is fixed to isolate such antibodies; the antibodies thus fixed can then be recovered by bringing the support into contact with a suitable solution, for example, of hydrochloric acid, glycin, urea or NaSCN.

The anti-$T_3$ and anti-$T_4$ antibodies used in the process according to the invention can be polyclonal or monoclonal antibodies.

Polyclonal antibodies can be obtained by hyperimmunization of sheep or rabbits using conjugated compounds of $T_3$ or $T_4$ with bovine serum albumin prepared, for example, by the carbodiimide method.

The immunoglobulins of the antiserum are collected by precipitation with caprylic acid by the method described by Steinbuch et al. in C.R. Soc. Biol. Paris 164, 296-301, 1970. The polyclonal antibodies can then be labelled with an enzyme, such as horse-radish peroxidase, using the sodium periodate method described by Wilson M. B. and Nakane P. K. in W. Knapp, K. Holubar, G. Wick (Eds.). Elsevier/North Holland Biomedical Press, 1978, pp. 215-224.

The Fab' fraction of the immunoglobulins of the antiserum can also be prepared by subjecting the purified IgGs to a pepsic digestion followed by a reduction with 2-mercapto ethyl amine. The Fab' fraction thus produced can then be labelled with an enzyme, such as horse-radish peroxidase, using the maleimide method described by Ishikawa et al.—J. Immunoassay, 1983, 4/3.

When monoclonal antibodies are used, they can be produced using the technique described by Kohler G and Milstein C. in Nature 256, pp. 495-497, 1975. In this technique thyroxine or triiodothyronine, for example, in the form of a $T_3$ or $T_4$/bovine serum albumin conjugate compound is injected into a mouse or some other suitable animal. The mouse is then sacrificed and cells taken from its spleen are fused with myeloma cells. The result is a hybrid cell called a "hybridoma" which reproduces itself in vitro. The population of hybridomas is so selected and manipulated as to isolate individual clones, each of which works out a single species of antibody in relation to the thyroxine or triiodothyronine injected.

BRIEF DESCRIPTION OF THE DRAWINGS

Other features and advantages of the invention will be more clearly gathered from a reading of the following examples given, of course, by way of illustrative, non-limitative examples, with reference to the accompanying drawings, in which FIG. 5 is a curve illustrating the determination of $T_4$ by the process according to the invention and FIG. 6 is a curve illustrating a determination of $T_4$ using labelled thyroglobulin.

EXAMPLE 1: DETERMINATION OF TOTAL $T_4$ THYROXINE

Figure 1:
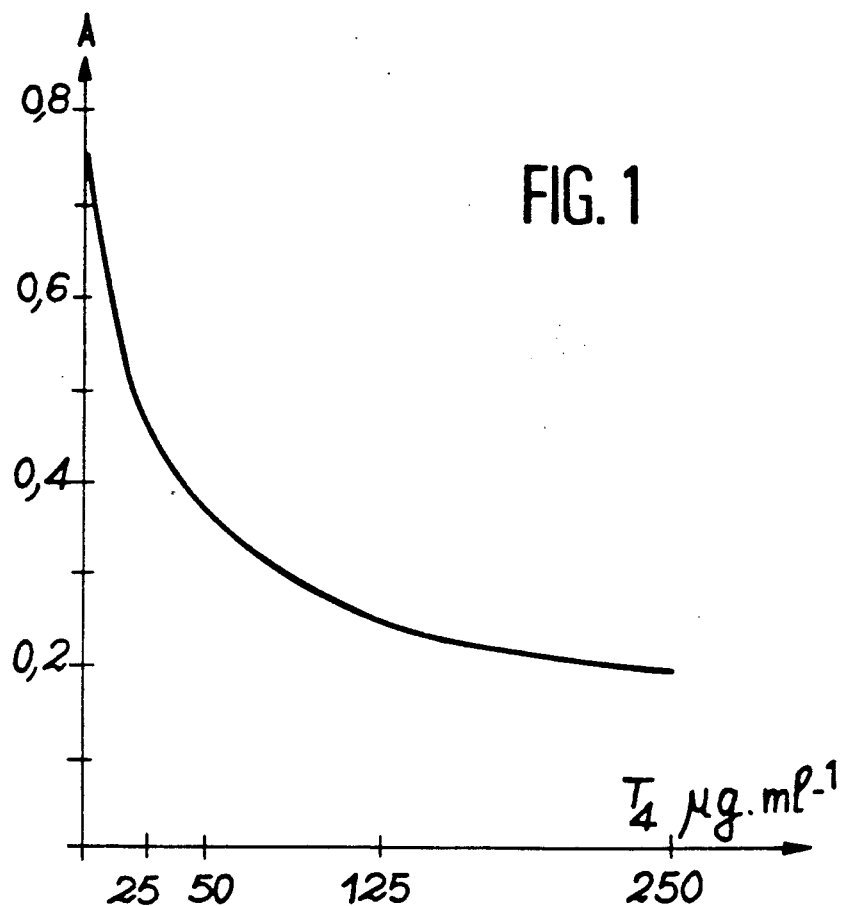
FIGS. 1 and 2 are curves illustrating the quantitative determination of $T_4$ thyroxine by the process according to the invention.

1. Preparation of the reagents (a) Preparation of the solid support containing thyroglobulin Bovine or porcine thyroglobulin was used which was produced or purified from the thyroid gland by the process disclosed in "Proceedings of the Society for Experimental Biology and Medicine", 29, (1931-32), which was dissolved at the rate of 5 mg/ml$^{-1}$ in a sodium phosphate buffer (0.1 mole$^{-1}$; pH 7.2) and preserved at $-20°$ C. The solid support was formed by a finned polyamide device having the shape of a 5-blade helix of surface area 2.5 cm$^2$, which was placed in a flat-bottom tube such as that disclosed in European Patent EP-A No. 0097573 in the name of the C.E.A.

To fix the thyroglobulin, first the thyroglobulin solution was diluted with the same phosphate buffer to obtain a concentration of 0.025 mg/ml$^{-1}$ and the tube was filled with the solution. After keeping it at ambient temperature for one night, the solution was withdrawn and the finned device was washed several times with the same phosphate buffer (0.1 mole/l$^{-1}$; pH 7.2) and preserved at 4° C. in the same buffer.

If bovine or porcine thyroglobulin is used, the quantity fixed on the fin is 2 $\mu$g.

(b) Preparation of anti-$T_4$ antibodies coupled to an enzyme formed by horse-radish peroxidase First a thyroxine immunogen/bovine serum albumin (BSA) conjugated compound was prepared by a catalyzed reaction by carbodiimide between the carboxylic and/or amine groups of the thyroxine and the amine and/or carboxylic groups of the bovine serum albumin.

To this end 20 mg $T_4$ were dissolved in 20 ml NaOH with 0.01 mole/l$^{-1}$, 10% dimethyl formamide was added, and then the solution was mixed with 40 mg bovine serum albumin. After dissolution, 80 mg 1-ethyl-3(3-dimethyl aminopropyl) carbodiimide was added and the pH was adjusted to 8.5 with 0.5N HCl. The mixture was allowed to incubate for 10 to 12 hours at ambient temperature, whereafter it was dialyzed for one night against a solution of NaCl at 140 mmole/l$^{-1}$. The result was a conjugated thyroxine/bovine serum albumin compound which was lyophilized and preserved at $-20°$ C.

Sheep were immunized by intradermal injections of 1 mg of the conjugated compound after it had been emulsified in Freund complete adjuvant. These injections were repeated every month for 8 months and blood was taken by puncturing the jugular vein. The antiserum titre was evaluated by radioimmunological quantitative determination. This titre is defined as being the final dilution capable of bonding 50% of the activity of a $T_4I^{125}$ tracer. An antiserum was obtained having a titre of 1/50 000 and a constant of affinity of $5.10^{-9}$ mole$^{-1}$.

A fraction enriched with IgG immunoglobulin was prepared from an anti-$T_4$ sheep serum by the caprylic acid method of Steinbuch and Audran, Archives of Biochemistry and Biophysics, 1969, 134, 279–284.

20 ml sodium acetate buffer (0.06 mole/l$^{-1}$; pH 4) and 0.68 ml caprylic acid (96% purity) was added to 10 ml of serum, the caprylic acid being added drop by drop with constant agitation. Agitation was maintained for 30 minutes at ambient temperature and the mixture was centrifuged for 10 minutes at 10 000 g. The supernatant containing the IgGs was filtered on paper, whereafter dialysis was performed for one night at 4° C. against a sodium phosphate buffer (17.5 mmole/l$^{-1}$; pH 6.5). In this way 400 mg of IgG was collected and purified by passing it over a cellulose column equilibrated with a sodium phosphate buffer (17.5% mmole/l$^{-1}$; pH 6.5). The purity of the IgG fraction collected was checked by electrophoresis against a rabbit/sheep antiprotein immunoserum. The result was purified IgGs having a degree of purity higher than 90%.

From this fraction of IgG, the conjugated anti-$T_4$/horse-radish peroxidase was formed by using the sodium periodate method described by M. B. Wilson and P. K. NAKANE in W. Knapp, K. HOLUBAR and G. WICK (Eds), Immunofluorescence and related staining techniques Elsevier/North Holland Biomedical Press, 1978, p. 215–224.

After the coupling reaction, reduction was performed by $NaBH_4$ and the conjugated compound was purified by precipitation with ammonium sulphate $(NH_2)_2SO_4$ and it was preserved in aliquot fractions at $-20°$ C. with 1% bovine serum albumin.

During utilization, the anti-$T_4$ IgG labelled with horse-radish peroxidase was diluted in a mixture containing 1% bovine serum albumin and ANS (0.04%) in phosphate buffer (0.1 mole/l$^{-1}$; pH 7.2).

(c) Preparation of the standard samples

To prepare the standard samples $T_4$ thyroxine in a concentration of 1 mg/ml was dissolved in 0.01N soda. Then the samples were diluted to obtain the required concentrations, using for the dilutions a pool of human serum freed from $T_4$ by carbon treatment at a rate of 100 mg/ml$^{-1}$ for one night at $+4°$ C., followed by two centrifugations and one filtration on a screen of 0.22 micrometer mesh.

2. Enzymoimmunological quantity determination (total $T_4$)

Volumes of 10 or 20 microliters of standard samples having $T_4$ concentrations of 0; 25; 50; 125; 250 $\mu$g/l$^{-1}$ and 20 mg/dl$^{-1}$ (white) were introduced into flat-bottom tubes each having a finned device coated with porcine thyroglobulin. Then 0.5 ml of anti-$T_4$ IgG labelled with horse-radish peroxidase, after having been diluted to 20 micrograms/ml in the aforedescribed diluting agent was introduced into each of the tubes. Incubation was performed for one hour at ambient temperature, whereafter the liquid phase present in each of the tubes was soaked up and the finned devices were washed twice with distilled water containing 0.05% Tween 20. The enzymatic activity connected with the fins was then determined by revealing it with the addition of 0.5 ml of the substrate solution formed by a sodium citrate phosphate buffer (0.1 mole/l$^{-1}$; pH 5.5) containing 5.5 mmole/l$^{-1}$ of oxygenated water and 3 g/l$^{-1}$ of orthophenylene diamine bichlorohydrate (final pH $5\pm0.1$) and the tubes were kept at ambient temperature in the dark for 30 minutes. The reaction was then stopped by the addition of 1 to 2 ml of 1N HCl, and absorbences were measured at 492 nm.

The results obtained are given in FIG. 1, which shows the development of absorbence at 492 nm as a function of the $T_4$ concentration of the samples, and corresponds to the calibration curve of the determination. This curve was used to determine the $T_4$ concentration of the sample to be determined.

In this example the determination was optimized by performing the same operations on standard samples with 0ng/ml$^{-1}$ of $T_4$, using finned devices having different concentrations of porcine or bovine thyroglobulin. The different concentrations were obtained by preparing the finned device by the same operating mode as that described above in 1(a), but using different thyroglobulin concentrations in the fixation solution.

Figure 2:
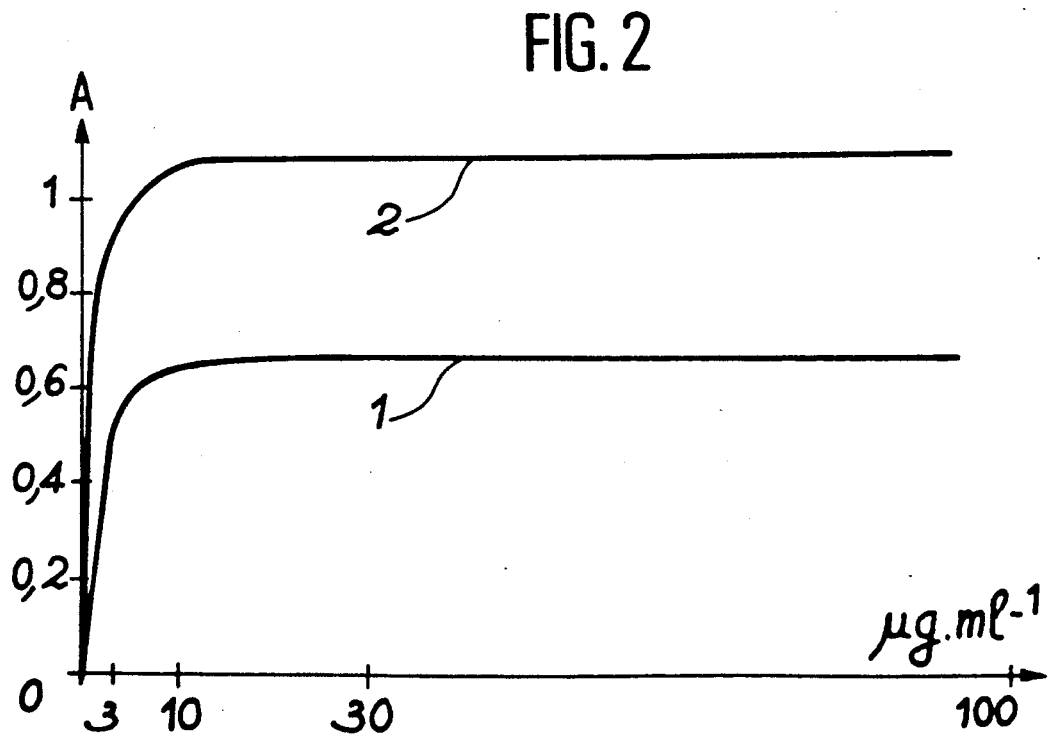

The results obtained are given in FIG. 2, which shows the absorbance at 492 nm as a function of the thyroglobulin concentration ($\mu$g/ml$^{-1}$) of the solution used for the preparation of the solid support. Curve 1 illustrates the results obtained with bovine thyroglobulin, while curve 2 illustrates the results obtained with porcine thyroglobulin.

A glance at FIG. 2 shows that the absorption plateau is obtained for concentrations close to 0.01 mg/ml$^{-1}$ in both cases.

A glance at FIG. 2 shows that porcine thyroglobulin has more capacity for fixing anti-$T_4$ antibodies than bovine thyroglobulin.

If these operations are repeated, using in the standard samples bovine or porcine thyroglobulin instead of $T_4$, the reaction equivalents in $T_4$ thyroxine of these two thyroglobulins can be calculated. It is thus found that bovine thyroglobulin contains 700 mg of $T_4$ per 5 mg of thyroglobulin—i.e., 0.14 mole of $T_4$ per mole of thyroglobulin.

In the case of porcine thyroglobulin, this contains the equivalent of 0.6 mole of $T_4$ per mole of thyroglobulin.

EXAMPLE 2: QUANTITATIVE DETERMINATION OF TOTAL $T_3$ TRIIODOTHYRONINE

In this example the same operating mode was followed as in example 1 to determine the triiodothyronine concentration of samples, using as anti-$T_3$ antibodies anti-$T_3$ IgGs coupled to horse-radish peroxidase obtained in the same way as the anti-$T_4$ IgGs coupled to horse-radish peroxidase.

The solid support was formed by balls of polystyrene coated with bovine thyroglobulin by immersion for one hour at 45° C. in a sodium phosphate buffer (0.1 mole/l$^{-1}$; pH 7.2) containing 0.1 mg/ml$^{-1}$ of bovine thyroglobulin. After several washings with the same buffer, the balls were preserved at $+4°$ C. in the same buffer containing 0.01% of Thimerosal. Before use, the balls were saturated with a 1% BSA solution in PBS (pH 7.2; 0.1 mole/l$^{-1}$) for half an hour.

The same diluting agents were used and the same method of preparing the standard samples.

For quantitative determination, 0.1 ml standard sample or sample for determination and 0.3 ml of anti-$T_3$ IgG labelled with horse-radish peroxidase diluted $\frac{1}{2}$ 000 in the diluting agent, corresponding to a dilution of 1:20 000 of the initial antiserum, and also the balls coated with bovine thyroglobulin were introduced into cupels. Incubation was performed for 2 hours at ambient temperature, whereafter the balls were extracted, washed three times with 5 ml of distilled water and transferred to throwaway polystyrene tubes. Then the enzymatic activity of the balls was determined, using the same operating mode as in example 1, but using only 0.3 ml of the substrate solution. As in example 1, the reaction was stopped after half an hour by the addition of 1 ml of 1N HCl.

The results obtained for various standard samples are given in FIG. 1, which shows the absorbance at 490 nm as a function of the $T_3$ concentration (in mg/ml$^{-1}$), corresponding to the $T_3$ calibration curve.

This curve can be used to determine the $T_3$ concentration of the sample.

Figure 4:
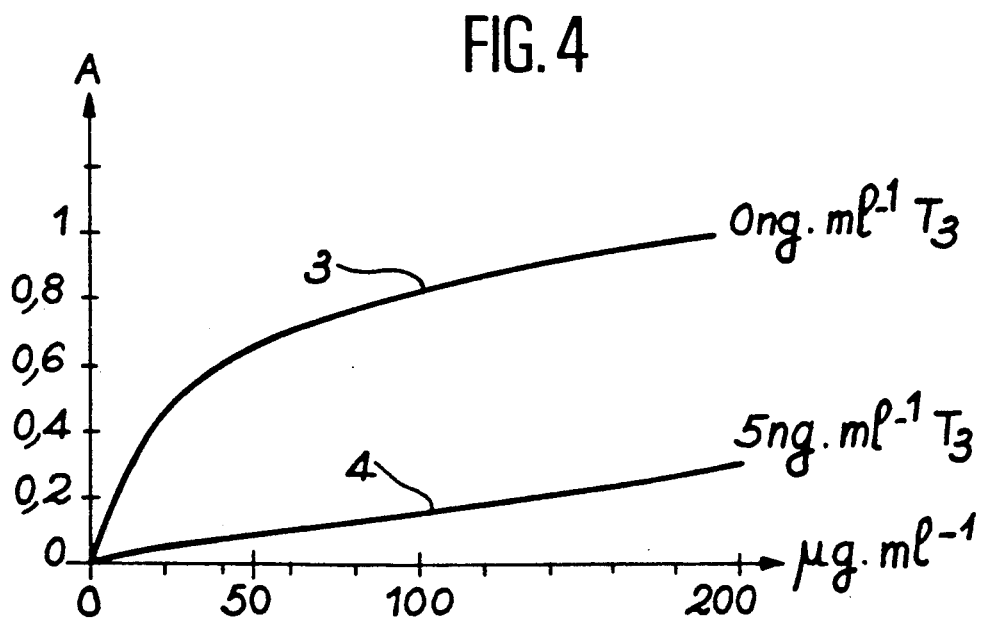

In this example determination was optimized by performing the same operations with standard samples containing either 0 mg/ml$^{-1}$ of $T_3$, or 5 mg/ml$^{-1}$ of $T_3$, using polystyrene balls having different bovine thyroglobulin concentrations. The results obtained are given in FIG. 4, in which curve 3 shows the variations in the absorbance of the samples with 0 mg/ml$^{-1}$ of $T_3$ as a function of the bovine thyroglobulin concentrations of the solution used for the preparation of the balls (in $\mu$g/ml$^{-1}$), while curve 4 shows the absorbance of the samples containing 5 mg/ml$^{-1}$ of $T_3$ as a function of the bovine thyroglobulin concentration of the solution used for the preparation of the balls (in $\mu$g/ml$^{-1}$).

Figure 3:
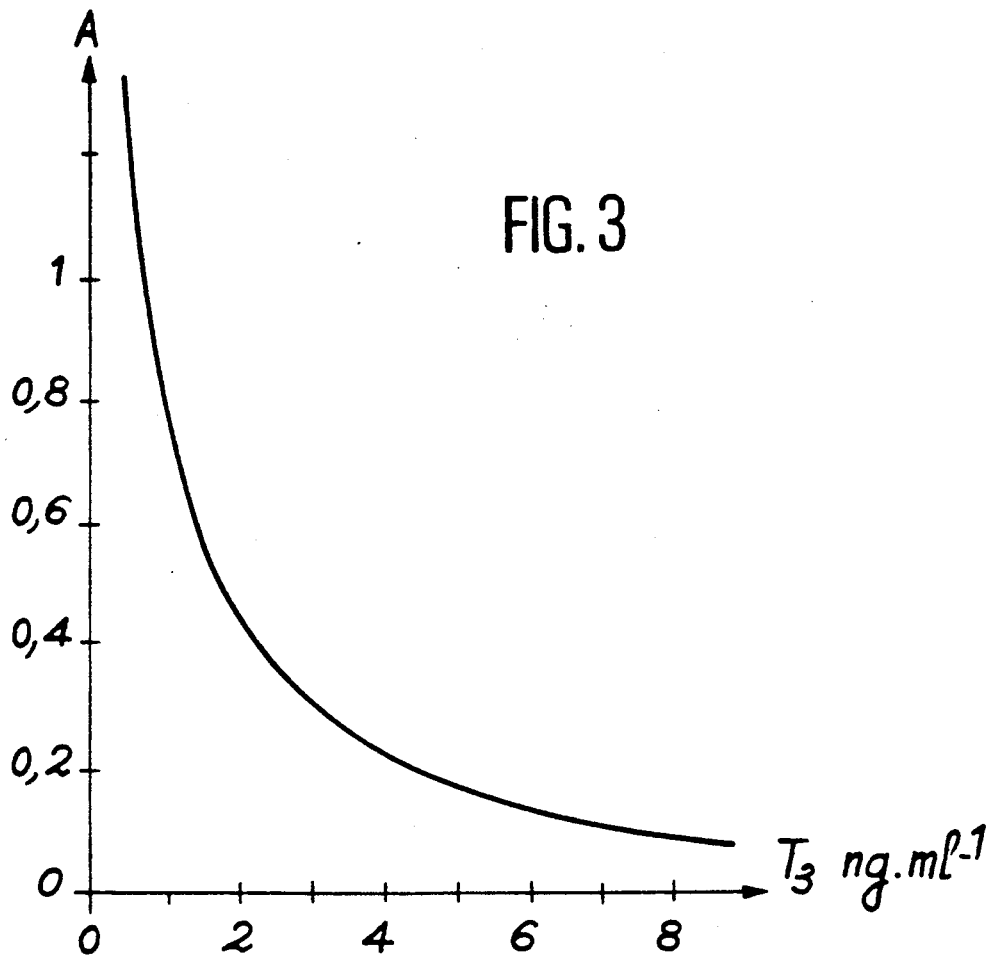
FIGS. 3 and 4 are curves illustrating the determination of $T_3$ triiodothyronine by the process according to the invention.

These operations were repeated as in example 1, using standard samples containing bovine thyroglobulin instead of triiodothyronine, the reaction equivalent in triiodothyronine of the bovine thyroglobulin being thus determined from the calibration curve in FIG. 3. In this way it was found that the bovine thyroglobulin contained the equivalent of 0.06 mole of $T_3$ per mole of bovine thyroglobulin.

The same operating mode was repeated, using a solid support formed by polystyrene balls coated with porcine thyroglobulin. The results obtained in these conditions were equivalent.

EXAMPLE 3: QUANTITATIVE DETERMINATION OF FREE $T_4$ THYROXINE

In this example the same operating mode was followed as in example 1, using polypropylene fins coated with porcine thyroglobulin. The standard samples were prepared as in example 1 over a range of 0–50 picograms of free $T_4$ per ml. Free $T_4$ calibration was performed by a reference technique.

The conjugated anti-$T_4$/enzyme compound was formed from the Fab' fraction of the antiserum produced by immunizing sheep, as in example 1. The Fab' fraction was obtained from the IgG produced in example 1 by pepsic digestion followed by a reduction using 2-mercapto ethyl amine. To perform pepsic digestion, 0.125 ml NaCl with 2 mole/l$^{-1}$ and 2 mg pepsine was added to 2.5 ml of IgG with 20 mg/ml$^{-1}$. The mixture was allowed to incubate for 24 hours at 37° C., and digestion was stopped by the addition of 1N soda, until a pH of 8 was obtained. After centrifugation, the supernatant was filtered on a Ultrogel ACA44 column and the fragments were eluted with a sodium phosphate buffer (0.1 mole/l$^{-1}$; pH 6). In this way 12 mg of Fab'$_2$ were collected in 20 ml and a 10-times concentration was performed with polyethylene glycol of molecular mass 35 000. Then the resulting Fab' fraction thus obtained was reduced by adding 0.22 ml of 2-mercapto ethyl amine with 0.1 mole.l$^{-1}$ in a sodium phosphate (0.1 mole/l$^{-1}$)/ethylene diamine tetraacetic acid (EDTA) (5 mmole/l$^{-1}$) buffer having a pH of 6. The mixture was allowed to incubate for one and a half hours at 37° C., whereafter the solution was filtered on a Sephadex G25 column with the same sodium phosphate/EDTA buffer. The result was 10.5 mg of the Fab' fraction.

This antibody fraction was then labelled with horse-radish peroxidase in the following manner.

First 14 mg horse-radish peroxidase were dissolved in 2.1 ml sodium phosphate buffer (0.1 mole/l$^{-1}$; pH 7). 7.5 mg N-succinimidyl-4-(N-maleimido methyl) cyclohexane-1-carboxylate was separately dissolved in 0.18 ml of dimethyl formamide. The two solutions were then mixed and allowed to incubate with agitation for 45 minutes at 30° C. After centrifugation, the supernatant was filtered on a Sephadex G25 column and elution was performed with a sodium phosphate buffer (0.1 mole/l$^{-1}$; pH 6) enabling a maleimide peroxidase solution to be obtained having a horse-radish peroxidase concentration of 5.2 mg/ml$^{-1}$. Then 10 mg of this solution was mixed in 1 ml of sodium phosphate buffer (0.1 mole/l$^{-1}$; pH 6) with 10.5 mg of Fab' fragments in 1 ml of EDTA (5 mmole/l$^{-1}$)/sodium phosphate (0.1 mole/l$^{-1}$) (pH 6) buffer and left to incubate for one hour at 30° C. The conjugated Fab'/horse-radish peroxidase compound was then filtered on an Ultrogel column and elution was performed with a sodium phosphate buffer (0.1 mole/l$^{-1}$; pH 6.5). The first peak corresponded to the conjugate, which had a molecular weight of 100 000. (Elution volume: 90 ml).

To perform quantitative determination, 0.05 ml of standard sample or sample to be determined and 0.5 ml of the anti-$T_4$ Fab' horse-radish peroxidase conjugate diluted to 300 nm/ml$^{-1}$ in a sodium phosphate buffer (0.1 mole/l$^{-1}$; pH 7.2) containing 0.1% of bovine serum albumin was introduced into tubes containing fins of polypropylene coated with porcine thyroglobulin. This was allowed to incubate for 3 hours at 37° C., whereafter the liquid was eliminated from the tubes and the fins were washed twice in distilled water. Then the enzymatic activity of the fins was determined by adding 0.5 ml of the substrate solution used in example 1, and incubation was performed for 30 minutes at ambient temperature. Then the reaction was stopped by the addition of 1 ml of 1N oxalic acid and the optical density was determined at 492 nm.

The results obtained are given in FIG. 5, which corresponds to the calibration curve of the determination.

EXAMPLE 4: QUANTITATIVE DETERMINATION OF THE TOTAL $T_4$ THYROXINE

For this quantitative determination, substantially the same operating mode was followed as in example 3, but using polystyrene balls coated with bovine thyroglobulin and the anti-$T_4$ antibodies labelled with the horse-radish peroxidase of example 1. For quantitative determination, 0.05 ml of standard sample or sample to be determined and 0.3 ml of the conjugated anti-$T_4$/horse-radish peroxidase diluted to 20 $\mu$g/ml in a sodium phosphate buffer (0.1 mole/l$^{-1}$; pH 7.2) containing 1% of SAB and 0.04% of ANS were introduced into tubes containing polystyrene balls. Incubation was performed for one hour at ambient temperature. The liquid was separated from the balls, and the latter were washed twice with distilled water. Then the enzymatic activity was determined by the addition of 0.3 ml of the substrate used in example 1 and incubation was performed for 30 minutes at ambient temperature. Then the reaction was stopped by the addition of 1 cm of 1N oxalic acid and the optical density was determined at 492 nm.

EXAMPLE 5: QUANTITATIVE DETERMINATION OF THE TOTAL $T_4$ THYROXINE

In this example determination was performed in the heterogeneous phase, using thyroglobulin labelled with an enzyme and anti-$T_4$ antibodies immobilized on a polypropylene solid support.

(a) Preparation of the Immobilized Anti-$T_4$ Antibodies

First of all the anti-$T_4$ antibodies, prepared in the same way as in example 1, were fixed on the polypropylene supports by immersing 100 supports in 100 ml of an anti-$T_4$ solution containing 0.03 mg/ml of anti-$T_4$ IgG, the reaction mixture being agitated for 18 hours at ambient temperature. Then the supports were washed with 1 l of pBS and covered with 0.1% BSA in pBS for 4 hours at ambient temperature. They were then rinsed with distilled water, lyophilized and stored in polyethylene bottles at ambient temperature.

(b) Preparation of the Labelled Thyroglobulin

Thyroglobulin labelled with horse-radish peroxidase was then prepared in the following manner. 100 mg of horse-radish peroxidase was activated with 1% glutaraldehyde, using the method of Avrameas and Ternynck described in Immunochemistry, vol. 8, p. 1175 (1971). Then the glutaraldehyde-activated horse-radish peroxidase was passed over a Sephadex G25 (2.5×20 cm) column balanced with a saline solution, and the fragments which were not of brown colour were collected. 1 ml of bicarbonate/carbonate solution (1M; pH 9.5) was added to 4.5 ml of the solution of activated horse-radish peroxidase, whereafter 3 mg of thyroglobulin dissolved in a bicarbonate/carbonate solution (1M, pH 9.5) was added drop by drop to the solution with agitation. The reaction mixture was agitated for 5 hours at ambient temperature and left overnight at 4° C. Then the solution of conjugated thyroglobulin/horse-radish peroxidase compound (2 ml) was concentrated by dialysis against polyethylene glycol PEG 35 000 sec. and the conjugate was purified by filtration on Sepharose 4B.

Then the conjugate compound was purified on a Sepharose column, elution being performed with a discontinuous gradient ranging from 0 to 50% ethylene glycol in a saline solution. The elution profile was checked by determining the enzymatic activity. The peaks containing the conjugated thyroglobulin/horse-radish peroxidase compound were stabilized by the addition of 1% BSA and 0.01% Thimerosal, mixed with an equal volume of glycerol, and stored at −20° C.

(c) Preparation of Standard Samples of $T_4$

These were prepared using the same operating mode as in example 1.

(d) Enzymoimmunological Quantitative Determination 0.025 ml of standard sample and 0.5 ml of the thyroglobulin/horse-radish peroxidase conjugate diluted in PB with 1% BSA and 0.04% ANS were introduced into polystyrene tubes containing the polypropylene supports coated with anti-$T_3$ antibodies. Incubation was performed for 1 hour at ambient temperature, whereafter the tubes were emptied and the polypropylene supports washed twice with 5 ml of distilled water containing 0.05% Tween 20. 0.5 ml of the freshly prepared substrate used in example 1 was then introduced into each tube and the tubes were kept at ambient temperature in the dark for 30 minutes. Then the enzymatic reaction was stopped by the addition of 1 ml of 1N oxalic acid and the absorbances were measured at 492 nm against a white which corresponded to a standard sample having a $T_4$ concentration of 200 mg per liter.

The results obtained with the standard sample are given in FIG. 6, which shows the absorbance at 490 nm as a function of the standard $T_4$ concentration (in $\mu g/l$), this giving the $T_4$ calibration curve.

This curve can then be used to determine the $T_4$ concentration of the sample by performing the same operations as before, determining absorbence at 490 nm, and referring to the calibration curve to discover the $T_4$ concentration corresponding to such absorbance.

What is claimed is:

1. A kit for the quantitative determination of $T_4$ thyroxine, which comprises:
   a series of tubes each comprising a solid phase coated under the same conditions with thyroglobulin, wherein thyroglobulin is first fixed on a solid support,
   a series of flasks containing standard samples of thyroxine, and
   a flask containing a labelled anti-$T_4$ antibody.

2. A kit for the quantitative determination of $T_3$ triiodothyronine, which comprises:
   a series of tubes each comprising a solid phased coated under the same conditions with thyroglobulin, wherein thyroglobulin is first fixed on a solid support,
   a series of flasks containing standard samples of $T_3$ triiodothyronine, and
   a flask containing a labelled anti-$T_3$ antibody.

3. A kit according to claim 1, wherein the anti-$T_4$ antibody is a conjugated compound formed by an anti-$T_4$ monoclonal antibody and the enzyme horse-radish peroxidase.

4. A kit according to claim 3, further comprising:
   at least one flask containing a chromogen for enzymatic developing,
   a flask containing a substrate buffer for enzymatic development, and
   a flask containing an acid able to stop the enzymatic reaction.

5. A kit according to claim 4, wherein the chromogen is the bischlorohydrate of o-phenylene diamine, and the acid is oxalic acid.

* * * * *